United States Patent
Eichhorn

(10) Patent No.: US 10,294,211 B2
(45) Date of Patent: *May 21, 2019

(54) PROCESS FOR ISOLATING AND PURIFYING AMBROX

(71) Applicant: Givaudan SA, Vernier (CH)

(72) Inventor: Eric Eichhorn, Zurich (CH)

(73) Assignee: Givaudan S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/568,535

(22) PCT Filed: Apr. 22, 2016

(86) PCT No.: PCT/EP2016/058997

§ 371 (c)(1),
(2) Date: Oct. 23, 2017

(87) PCT Pub. No.: WO2016/170106

PCT Pub. Date: Oct. 27, 2016

(65) Prior Publication Data

US 2018/0134678 A1  May 17, 2018
US 2018/0346434 A9  Dec. 6, 2018

(30) Foreign Application Priority Data

Apr. 24, 2015 (GB) .................. 1507170.7

(51) Int. Cl.
| | | |
|---|---|---|
| *C07D 307/92* | (2006.01) | |
| *C12P 17/04* | (2006.01) | |
| *C11B 9/00* | (2006.01) | |
| *B01D 9/00* | (2006.01) | |
| *C07B 63/00* | (2006.01) | |

(52) U.S. Cl.
CPC ........... *C07D 307/92* (2013.01); *B01D 9/005* (2013.01); *C07B 63/00* (2013.01); *C11B 9/0076* (2013.01); *C12P 17/04* (2013.01); *C12Y 504/99017* (2013.01); *C07B 2200/09* (2013.01)

(58) Field of Classification Search
CPC ... C07D 307/92; C07B 63/00; C07B 2200/09; B01D 9/005; C11B 9/0076; C12Y 504/99017; C12P 17/04
USPC ....................................................... 549/458
See application file for complete search history.

(56) References Cited

U.S. PATENT DOCUMENTS

| 6,524,831 B2 | 2/2003 | Steinbüchel et al. |
| 8,759,043 B2 | 6/2014 | Breuer et al. |
| 2003/0092143 A1 | 5/2003 | Rabenhorst et al. |
| 2009/0117557 A1 | 5/2009 | Wang et al. |
| 2012/0135477 A1 | 5/2012 | Breuer et al. |
| 2012/0237991 A1 | 9/2012 | Breuer et al. |
| 2013/0273619 A1 | 10/2013 | Bonnekessel et al. |
| 2016/0304911 A1 | 10/2016 | Sato et al. |
| 2018/0148751 A1* | 5/2018 | Eichhorn ............... C12N 9/90 |

FOREIGN PATENT DOCUMENTS

| CN | 105 037 308 A | 11/2015 |
| EP | 2 438 182 A2 | 12/2010 |
| JP | 2009-060799 A | 3/2009 |
| JP | 2013-132226 A | 7/2013 |
| JP | 2017-074053 A | 4/2017 |
| WO | WO 2004/063699 A2 | 7/2004 |
| WO | WO 2010/139710 A1 | 12/2010 |
| WO | WO 2010/139719 A2 | 12/2010 |
| WO | WO 2012/066059 A2 | 5/2012 |

(Continued)

OTHER PUBLICATIONS

Escher et al, configuration—Odor Relationships in 5 beta-Ambrox, Helvetica Chimica Acta, 1990, vol. 73, p. 1935-1947. (Year: 1990).*

(Continued)

*Primary Examiner* — Taylor V Oh

(74) *Attorney, Agent, or Firm* — Curatolo Sidoti Co., LPA; Salvatore A. Sidoti; Floyd Trillis, III

(57) ABSTRACT

A method of isolating and purifying (−)-Ambrox from a reaction mixture comprising (−)-Ambrox and one or more of the compounds (II), (III) and (IV)

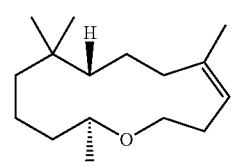

(II)

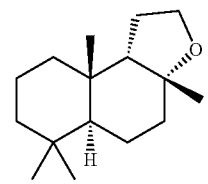

(III)

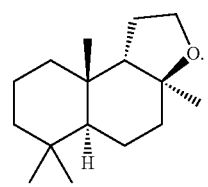

(IV)

23 Claims, No Drawings

Specification includes a Sequence Listing.

(56) References Cited

FOREIGN PATENT DOCUMENTS

| WO | WO 2015/033746 A1 | 3/2015 |
| WO | WO 2015/059290 A1 | 4/2015 |
| WO | WO 2015/059293 A1 | 4/2015 |

OTHER PUBLICATIONS

PCT/EP2016/058997—International Search Report, dated Jun. 22, 2016.
PCT/EP2016/058997—International Written Opinion, dated Jun. 22, 2016.
Great Britain Search Report GB 1507170.7, dated Jan. 28, 2016.
Decorzant, et al., "A Short Synthesis of Ambrox® from Sclareol", Tetrahedron, Jan. 1, 1987, vol. 43, No. 8, pp. 1871-1879, Elsevier Science Publishers, Amsterdam, Netherlands.
Leffingwell, et al., "Biotechnology-Conquests and Challenges in Flavors and Fragrances", Leffingwell Reports, Mar. 1, 2015, vol. 7, No. 2, pp. 1-11.
Seitz et al., "Substrate specificity of a novel squalene-hopene cyclase from Zymomonas mobilis", J. Molecular Catalysis B: Enzymatic, Dec. 2012, vol. 84, pp. 72-77. (Only Abstract provided).

* cited by examiner

SEQUENCE LISTING

<160> NUMBER OF SEQ ID NOS: 4

<210> SEQ ID NO 1
<211> LENGTH: 631
<212> TYPE: PRT
<213> ORGANISM: Alicyclobacillus acidocaldarius

<400> SEQUENCE: 1

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

```
Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
 50                  55                  60

Arg Arg Tyr Leu Leu His Glu Gln Arg Glu Asp Gly Thr Trp Ala Leu
 65              70                  75                  80

Tyr Pro Gly Gly Pro Pro Asp Leu Asp Thr Thr Ile Glu Ala Tyr Val
                 85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
            115                 120                 125

Phe Thr Arg Met Trp Leu Ala Leu Val Gly Tyr Pro Trp Glu Lys
        130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
            195                 200                 205

Gly Ala Lys Gly Gly Gly Trp Ile Phe Asp Ala Leu Asp Arg Ala
        210                 215                 220

Leu His Gly Tyr Gln Lys Leu Ser Val His Pro Phe Arg Ala Ala
225                 230                 235                 240

Glu Ile Arg Ala Leu Asp Trp Leu Leu Glu Arg Gln Ala Gly Asp Gly
            245                 250                 255

Ser Trp Gly Gly Ile Gln Pro Pro Trp Phe Tyr Ala Leu Ile Ala Leu
                260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
        290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
        370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445
```

```
Thr Ala His Val Leu Glu Cys Phe Gly Ser Phe Gly Tyr Asp Asp Ala
        450                 455                 460
Trp Lys Val Ile Arg Arg Ala Val Glu Tyr Leu Lys Arg Glu Gln Lys
465                 470                 475                 480
Pro Asp Gly Ser Trp Phe Gly Arg Trp Gly Val Asn Tyr Leu Tyr Gly
                485                 490                 495
Thr Gly Ala Val Val Ser Ala Leu Lys Ala Val Gly Ile Asp Thr Arg
            500                 505                 510
Glu Pro Tyr Ile Gln Lys Ala Leu Asp Trp Val Glu Gln His Gln Asn
        515                 520                 525
Pro Asp Gly Gly Trp Gly Glu Asp Cys Arg Ser Tyr Glu Asp Pro Ala
530                 535                 540
Tyr Ala Gly Lys Gly Ala Ser Thr Pro Ser Gln Thr Ala Trp Ala Leu
545                 550                 555                 560
Met Ala Leu Ile Ala Gly Gly Arg Ala Glu Ser Ala Ala Arg Arg
                565                 570                 575
Gly Val Gln Tyr Leu Val Glu Thr Gln Arg Pro Asp Gly Gly Trp Asp
            580                 585                 590
Glu Pro Tyr Tyr Thr Gly Thr Gly Phe Pro Gly Asp Phe Tyr Leu Gly
                595                 600                 605
Tyr Thr Met Tyr Arg His Val Phe Pro Thr Leu Ala Leu Gly Arg Tyr
        610                 615                 620
Lys Gln Ala Ile Glu Arg Arg
625                 630

<210> SEQ ID NO 2
<211> LENGTH: 631
<212> TYPE: PRT
<213> ORGANISM: Artificial sequence
<220> FEATURE:
<223> OTHER INFORMATION: Synthetic AacSHC Derivative

<400> SEQUENCE: 2

Met Ala Glu Gln Leu Val Glu Ala Pro Ala Tyr Ala Arg Thr Leu Asp
1               5                   10                  15
Arg Ala Val Glu Tyr Leu Leu Ser Cys Gln Lys Asp Glu Gly Tyr Trp
            20                  25                  30
Trp Gly Pro Leu Leu Ser Asn Val Thr Met Glu Ala Glu Tyr Val Leu
        35                  40                  45
Leu Cys His Ile Leu Asp Arg Val Asp Arg Asp Arg Met Glu Lys Ile
    50                  55                  60
Arg Arg Tyr Leu Leu His Glu Gln Arg Glu Asp Gly Thr Trp Ala Leu
65                  70                  75                  80
Tyr Pro Gly Gly Pro Pro Asp Leu Asp Thr Thr Ile Glu Ala Tyr Val
                85                  90                  95
Ala Leu Lys Tyr Ile Gly Met Ser Arg Asp Glu Glu Pro Met Gln Lys
            100                 105                 110
Ala Leu Arg Phe Ile Gln Ser Gln Gly Gly Ile Glu Ser Ser Arg Val
        115                 120                 125
Phe Thr Arg Met Trp Leu Ala Leu Val Gly Tyr Pro Trp Glu Lys
    130                 135                 140
Val Pro Met Val Pro Pro Glu Ile Met Phe Leu Gly Lys Arg Met Pro
145                 150                 155                 160
Leu Asn Ile Tyr Glu Phe Gly Ser Trp Ala Arg Ala Thr Val Val Ala
                165                 170                 175
```

```
Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Trp Ile Phe Asp Ala Leu Asp Arg Ala
        210                 215                 220

Leu His Gly Tyr Gln Lys Leu Ser Val His Pro Phe Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
            290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
        450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
            530                 535                 540

Tyr Ala Gly Lys Gly Ala Ser Thr Pro Ser Gln Thr Ala Trp Ala Leu
545                 550                 555                 560

Met Ala Leu Ile Ala Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Tyr Pro Gly Asp Phe Tyr Leu Gly
```

```
                595                 600                 605
            Tyr Thr Met Tyr Arg His Val Phe Pro Thr Leu Ala Leu Gly Arg Tyr
                610                 615                 620
            Lys Gln Ala Ile Glu Arg Arg
            625                 630

<210> SEQ ID NO 3
<211> LENGTH: 1896
<212> TYPE: DNA
<213> ORGANISM: Artificial sequence
<220> FEATURE:
<223> OTHER INFORMATION: Synthetic AacSHC Derivative

<400> SEQUENCE: 3
atggctgagc agttggtgga agcgccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc cacattctcg atcgcgtcga tcgggatcgc     180
atggagaaga tccggcggta cctgttgcac gagcagcgcg aggacggcac gtgggccctg     240
tacccgggtg gccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa cgcatgccg     480 ctcaacatct acgagtttgg ctcgtgggct cgggcgaccg tcgtggcgct ctcgattgtg     540
atgagccgcc agccggtgtt cccgctgccc gagcgggcgc gcgtgcccga gctgtacgag     600
accgacgtgc ctccgcgccg gcgcggtgcc aagggagggg gtgggtggat cttcgacgcg     660
ctcgaccggg cgctgcacgg gtatcagaag ctgtcggtgc acccgttccg ccgcgcggcc     720
gagatccgcg ccttggactg gttgctcgag cgccaggccg agacggcag ctggggcggg     780 attcagccgc cttggttta cgcgctcatc gcgctcaaga ttctcgacat gacgcagcat     840
ccggcgttca tcaagggctg ggaaggtcta gagctgtacg gcgtggagct ggattacgga     900
ggatggatgt tcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat ccgctggat tgtcggcatg cagagctcga acggcggttg ggcgcctac    1260 gacgtcgaca cacgagcga tctcccgaac cacatcccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttgggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcacccgt cgcagacggc ctgggcgctg    1680
atggcgctca tcgcgggcgg cagggcggag tccgaggccg cgccgcgg cgtgcaatac    1740 ctcgtggaga cgcagcgccc ggacggcggc tgggatgagc cgtactacac cggcacgggc    1800
ttcccagggg attggtacct cggctacacc atgtaccgcc acgtgtttcc gacgctcgcg    1860
```
ctcggccgct acaagcaagc catcgagcgc aggtga                           1896

<210> SEQ ID NO 4
<211> LENGTH: 631
<212> TYPE: PRT
<213> ORGANISM: Artificial sequence
<220> FEATURE:
<223> OTHER INFORMATION: Synthetic AacSHC Derivative

<400> SEQUENCE: 4

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65              70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Ala Ala
225             230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

```
Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
        370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
        450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Trp Tyr Leu Gly
        595                 600                 605

Tyr Thr Met Tyr Arg His Val Phe Pro Thr Leu Ala Leu Gly Arg Tyr
        610                 615                 620

Lys Gln Ala Ile Glu Arg Arg
625                 630
```

PROCESS FOR ISOLATING AND PURIFYING AMBROX

CROSS REFERENCE TO RELATED APPLICATIONS

This application is a national stage application of International Application No. PCT/EP2016/058997, filed 22 Apr. 2016, which claims priority from Great Britain patent application Ser. No. 1507170.7, filed 24 Apr. 2015, which applications are incorporated herein by reference.

SEQUENCE LISTING

Attached to this Amendment is a Sequence Listing as filed in the International application. The Sequence Listing includes sequences for SEQ ID NOS: 1-4. Please add the Sequence Listing to the present application.

The present invention is concerned with a method of preparing, isolating and purifying the isomer (−)-Ambrox. More particularly, the invention is concerned with a method of preparing (−)-Ambrox by means of a bioconversion, as well as to a method of its recovery and purification from a reaction mixture.

AMBROFIX™ is the proprietary Givaudan trade name of the enantiomerically pure compound (−)-Ambrox, which has the general formula (I).

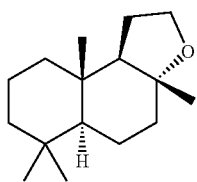

(I)

AMBROFIX™ is a very important molecule in the perfumers' palette of ingredients. It delivers a highly powerful, highly substantive and highly stable ambery note for use in all perfumery applications. AMBROFIX™, available from Givaudan, is the most suitable material for obtaining an authentic ambergris odour note.

Currently, AMBROFIX™ is produced synthetically from starting materials of natural origin. The availability and quality of certain starting materials are dependent on climatic conditions, as well as socio-economic factors. Furthermore, since starting materials may be extracted from natural resources, with modest yields, they are available at prices that will, in all likelihood, increasingly render their use uneconomical on an industrial scale. Accordingly, if commercial industrial supplies of AMBROFIX™ are to continue to be available at a reasonable cost, there is a need for a more cost-effective process of production and purification, which is capable of industrialization.

An industrially scalable biotechnological route into AMBROFIX™ would be attractive because it is potentially less complex and less polluting than fully synthetic procedures.

A potentially useful substrate on which to attempt a bioconversion to provide (−)-Ambrox is homofarnesol. In their seminal paper, Neumann et al (Biol. Chem. Hoppe-Seyler Vol. 367 pp 723-726 (1986)) discussed the feasibility of converting homofarnesol to (−)-Ambrox under enzymatic catalysis, employing the enzyme Squalene Hopene Cyclase (SHC). The homofarnesol employed was a mixture of the four geometric isomers of this molecule. Of the four isomers, only the 7E,3E geometric isomer (using conventional nomenclature) could be cyclized, and then only with very low yield of the desired (−)-Ambrox.

JP 2009-60799 (Kao) discloses a synthesis whereby SHC acts on a homofarnesol substrate to produce (−)-Ambrox. The substrate is a mixture of all four geometric isomers (3Z,7Z; 3E,7Z; 3Z,7E; and 3E,7E). The document only discloses the preparation of (−)-Ambrox from homofarnesol extracts containing SHC. The homofarnesol mixture is converted to (−)-Ambrox and its 9-epi stereoisomer, and purification can be carried out by distillation or by column chromatography. Kao does not describe a process whereby homofarnesol is converted into (−)-Ambrox using intact microorganisms producing SHC, and furthermore, it does not provide any technical teaching related to the downstream processing of complex reaction mixtures obtained by such processes that can yield (−)-Ambrox in olfactively pure form.

To the applicant's knowledge, the prior art does not describe any viable, industrially scalable processes, involving the SHC-catalyzed bioconversion of homofarnesol, to provide (−)-Ambrox in olfactively pure form.

Furthermore, if bioconversion of homofarnesol is to be realized on an industrial scale, cost-efficient sources of highly pure, 3E,7E-homfarnesol should be available. However, although synthetic routes into homofarnesol have been described in the literature (see for example US 2013/0273619), to the applicant's knowledge there are no cost-effective, industrial-scale sources of pure 7E,3E-homofarnesol currently available.

There remains a need to provide an economically feasible and industrially scalable route into the valuable fragrance ingredient (−)-Ambrox.

In co-pending patent applications PCT/EP2014/072891 (published as WO2015/059293) and PCT2014/EP/072882 (published as WO2015/059290), the applicant describes an efficient method of preparing 7E,3E/Z-homofarnesol mixture that is enriched in the 7E,3E geometric isomer. The 7E,3E/Z-homofarnesol mixture is prepared from beta-farnesene, and the isomeric information contained in this starting material is preserved, such that the homofarnesol double bond at the 7-position is fixed in the E-configuration. However, even 30 this elegant chemistry still results in a 3E/Z isomer mixture. Pure 7E,3E-homofarnesol remains synthetically challenging, and might only be achieved by means of economically disadvantageous purification of isomeric mixtures.

Surprisingly, the applicant has found that 7E,3E/Z-homofarnesol mixtures can undergo a bioconversion process, whereby the homofarnesol mixture is enzymatically cyclized in the presence of a recombinant microorganism expressing an enzyme, in particular a Squalene Hopene Cyclase (SHC) biocatalyst capable of bioconverting homofarnesol to (−)-Ambrox, to yield a reaction mixture from which (−)-Ambrox can be isolated in olfactively pure form with surprisingly facile downstream processing.

In one aspect of the invention there is provided the enzyme-catalyzed cyclisation of homofarnesol to provide a reaction mixture comprising (−)-Ambrox, wherein the homofarnesol comprises a mixture of 7E,3E/Z-geometric isomers of homofarnesol, and wherein the reaction is carried out in the presence of a recombinant microorganism producing the enzyme, more particularly an intact recombinant microorganism producing the enzyme.

In an embodiment of the invention, the cyclization reaction is carried out in the presence of an SHC biocatalyst capable of bioconverting homofarnesol to (−)-Ambrox.

The SHC biocatalyst is a wild-type or a variant enzyme or is a microorganism expressing a gene encoding the SHC enzyme, preferably a recombinant *E. coli* microorganism. The SHC biocatalyst can be used in any form such as but not limited to a purified SHC enzyme, a crude extract containing an SHC enzyme or an immobilised SHC enzyme (e.g. on a carrier), or the biocatalyst can be a microorganism having produced or producing the SHC enzyme, such as an intact recombinant whole cell and/or fragmented cell or a membrane fraction containing the SHC enzyme.

In a particular embodiment of the present invention, the homofarnesol mixture is enriched in the 7E,3E-geometric isomer.

In a more particular embodiment, the homofarnesol mixture is at least 55/45 by weight 7E,3E/7E,3Z.

In a more particular embodiment, the homofarnesol mixture is at least 70/30 by weight 7E,3E/7E,3Z.

In a still more particular embodiment, the homofarnesol mixture is at least 80/20 by weight 7E,3E/7E,3Z In a still more particular embodiment, the homofarnesol mixture is at least 90/10 by weight 7E,3E/7E,3Z.

In a still more particular embodiment, the homofarnesol mixture is at least 95/5 by weight 7E,3E/7E,3Z.

In a particular embodiment of the present invention, the homofarnesol mixture consists of 7E,3E/Z-geometric isomers and no other geometric isomers of homofarnesol.

The skilled person understands that the term 7E, 7Z, 3E or 3Z used in connection with homofarnesol refers respectively to the orientation of the double bond at the 7-position and 3-position of homofarnesol. The 7E,3E-homofarnesol compound has the CAS No. 459-89-2, whereas the 7E,3Z-homofarnesol compound has the CAS No. 138152-06-4. The use of the term 7E, 3E/Z-homofarnesol refers to a mixture of the compounds.

Methods of obtaining homofarnesol mixtures useful as a substrate in the cyclisation reaction in accordance with the method of the present invention are set forth in the co-pending applications PCT/EP2014/072891 (published as WO2015/059293) and PCT2014/EP/072882 (published as WO2015/059290) referred to above, which are hereby incorporated by reference in their entirety. In general terms, they describe a synthesis of homofarnesol mixtures that proceeds by converting farnesene, more particularly alpha-farnesene and/or beta-farnesene, to its corresponding cyclopropanated farnesene derivative, using an organic solution of an N-alkyl-N-nitroso urea. The cyclopropanated derivative then undergoes ring-opening and rearrangement reactions in the presence of a Bronsted acid to afford the homofarnesol mixture, which is selective for the 7E,3E geometric isomer. Using farnesene, as a starting material is particularly preferred because it ensures that the E-configuration of the double bond at the 7 position of homofarnesol is fixed.

Specific reaction conditions, which form particular embodiments of the present invention, are set forth in the co-pending applications, as well as the examples hereinbelow, and do not require more elaboration here.

The cyclization of homofarnesol to provide a reaction mixture containing (−)-Ambrox may be catalysed by Squalene Hopene Cyclase (SHC). SHC may be a wild type enzyme (e.g. SEQ ID No. 1), or a variant thereof (e.g. SEQ ID No. 2, or SEQ ID No. 4). SHC can be obtained from *Alicyclobacillus acidocaldarius* (*Bacillus acidocaldarius*), *Zymomonas mobilis* or *Bradyrhizobium japonicum* (as set forth in Example 3b of US20120135477A1).

However, the enzyme can also be produced by recombinant means, using techniques that are generally known in the art.

The term "recombinant" as used with respect to the production of enzymes shall refer to enzymes produced by recombinant DNA techniques, i.e., produced from cells transformed by an exogenous DNA construct encoding the desired enzyme. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

Nucleic acid molecule(s) is/are operatively linked to expression control sequences allowing expression in prokaryotic and/or eukaryotic host cells. As used herein, "operatively linked" means incorporated into a genetic construct so that expression control sequences effectively control expression of a coding sequence of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression or which allow inducible expression like, for example, CUP-1 promoter, the tet-repressor as employed, for example, in the tet-on or tet-off systems, the lac system, the trp system regulatory elements. By way of example, Isopropyl β-D-1-thiogalactopyranoside (IPTG) is an effective inducer of protein expression in the concentration range of 100 μM to 1.0 mM. This compound is a molecular mimic of allolactose, a lactose metabolite that triggers transcription of the lac operon, and it is therefore used to induce protein expression where the gene is under the control of the lac operator.

Similarly, nucleic acid molecule(s) can form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

Recombinant polynucleotides can encode SHC enzymes such as the wild type SHC or a variant thereof, which may be inserted into a vector for expression and optional purification. One type of vector is a plasmid representing a circular double stranded DNA loop into which additional DNA segments are ligated. Certain vectors can control the expression of genes to which they are functionally linked. These vectors are called "expression vectors". Usually expression vectors suitable for DNA recombination techniques are of the plasmid type. Typically, an expression vector comprises a gene such as the wild type SHC or a variant thereof. In the present description, the terms "plasmid" and "vector" are used interchangeably since the plasmid is the vector type most often used.

Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host is augmented through the stable introduction of one or more recombinant genes. However, autonomous or replicative plasmids or vectors can also be used within the scope of this disclosure. Moreover, the present disclosure can be practiced using a low copy number, e.g., a single copy, or high copy number plasmid or vector.

In a preferred embodiment the vector of the present disclosure comprises plasmids, phagemids, phages, cosmids, artificial bacterial and artificial yeast chromosomes, knock-out or knock-in constructs. Synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are produced within the cell upon introduction of the vector. The diverse gene substrates may be incorporated into plasmids. The plasmids are often standard cloning vectors, e.g., bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more of the following nucleotide sequences as is well known in the art. For in vivo recombination, the gene to be recombined with the genome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transformed cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which can be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which can be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp, yeast host cells, such as *S. cerevisiae,* insect host cells, such as *Spodoptora frugiperda* or human host cells, such as HeLa and Jurkat.

Specifically, the cell is a eukaryotic cell, preferably a fungal, mammalian or plant cell, or prokaryotic cell. Suitable eucaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli*.

Preferably prokaryotes, such as *E. coli, Bacillus, Streptomyces,* or mammalian cells, like HeLa cells or Jurkat cells, or plant cells, like *Arabidopsis*, may be used.

Preferably the cell is an *Aspergillus* sp or a fungal cell, preferably, it can be selected from the group consisting of the genera *Saccharomyces, Candida, Kluyveromyces, Hansenula, Schizosaccharomyces, Yarrowia, Pichia* and *Aspergillus*.

Preferably the *E. coli* host cell is an *E. coli* host cell which is recognized by the industry and regulatory authorities (including but not limited to an *E. coli* K12 host cell or as demonstrated in the Examples, an *E. coli* BL21 host cell).

One preferred host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

In one embodiment, the recombinant *E. coli* microorganism comprises nucleotide sequences encoding SHC genes or functional equivalents/homologies thereof including but not limited to variants, homologues mutants, derivatives or fragments thereof.

Another preferred host cell to use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells is performed, in a conventional manner. The culture medium contains a carbon source, at least one nitrogen source and inorganic salts, and vitamins are added to it. The constituents of this medium can be the ones which are conventionally used for culturing the species of microorganism in question.

Carbon sources of use in the instant method include any molecule that can be metabolized by the recombinant host cell to facilitate growth and/or production of (−)-Ambrox. Examples of suitable carbon sources include, but are not limited to, sucrose (e.g., as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

The suitability of a recombinant host cell microorganism for use in the methods of the present disclosure may be determined by simple test procedures using well known methods. For example, the microorganism to be tested may be propagated in a rich medium (e.g., LB-medium, Bactotryptone yeast extract medium, nutrient medium and the like) at a pH, temperature and under aeration conditions commonly used for propagation of the microorganism. Once recombinant microorganisms (i.e. recombinant host cells) are selected that produce the desired products of bioconversion, the products are typically produced by a production host cell line on the large scale by suitable expression systems and fermentations, e.g. by microbial production in cell culture.

In one embodiment of the present disclosure, a defined minimal medium such as M9A is used for cell cultivation. The components of M9A medium comprise: 14 g/L $KH_2PO_4$, 16 g/L $K_2HPO_4$, 1 g/L $Na_3Citrate.2H_2O$, 7.5 g/L $(NH_4)_2SO_4$, 0.25 g/L $MgSO_4.7H_2O$, 0.015 g/L $CaCl_2.2H_2O$, 5 g/L of glucose and 1.25 g/L yeast extract).

In another embodiment of the present disclosure, nutrient rich medium such as LB (Luria-Bertani) was used. The components of LB comprise: 10 g/L tryptone, 5 g/L yeast extract, 5 g/L NaCl).

Other examples of Mineral Medium and M9 Mineral Medium are disclosed, for example, in U.S. Pat. No. 6,524,831B2 and US 2003/0092143A1.

The recombinant microorganism may be grown in a batch, fed batch or continuous process or combinations thereof. Typically, the recombinant microorganism is grown in a fermentor at a defined temperature in the presence of a suitable nutrient source, e.g., a carbon source, for a desired period of time to bioconvert homofarnesol to (−)-Ambrox in a desired amount.

The recombinant host cells may be cultivated in any suitable manner, for example by batch cultivation or fed-batch cultivation. As used herein, the term "batch cultivation" is a cultivation method in which culture medium is neither added nor withdrawn during the cultivation. As used herein, the term "fed-batch" means a cultivation method in which culture medium is added during the cultivation but no culture medium is withdrawn.

One embodiment of the present disclosure provides a method of producing (−)-Ambrox in a cellular system comprising producing wild type SHC or variants thereof under suitable conditions in a cellular system, feeding homofarnesol to the cellular system, converting the homofarnesol to (−)-Ambrox using the SHC or variants produced using the cellular system, collecting (−)-Ambrox from cellular system and isolating the (−)-Ambrox from the system. Expression of other nucleotide sequences may serve to enhance the method. The bioconversion method can include the additional expression of other nucleotide sequences in the cellular system. The expression of other nucleotide sequences may enhance the bioconversion pathway for making (−)-Ambrox.

A further embodiment of the present disclosure is a bioconversion method of making (−)-Ambrox comprising growing host cells comprising wild type SHC or variant genes, producing wild type SHC or variant enzymes in the host cells, feeding homofarnesol (e.g. EEH) to the host cells, incubating the host cells under conditions of pH, temperature and solubilizing agent suitable to promote the conversion of homofarnesol to Ambrox and collecting (−)-Ambrox. The production of the wild type SHC or variant enzymes in the host cells provides a method of making (−)-Ambrox when homofarnesol is added to the host cells under suitable reaction conditions. Achieved conversion may be enhanced by adding more biocatalyst and SDS to the reaction mixture.

The recombinant host cell microorganism may be cultured in a number of ways in order to provide cells in suitable amounts expressing the wild type SHC or variant enzymes for the subsequent bioconversion step. Since the microorganisms applicable for the bioconversion step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent bioconversion step of the present disclosure. Typically the cells are grown to a particular density (measurably as optical density (OD)) to produce a sufficient biomass for the bioconversion reaction. The cultivation conditions chosen influence not only the amount of cells obtained (the biomass) but the quality of the cultivation conditions also influences how the biomass becomes a biocatalyst. The recombinant host cell microorganism expressing the wild type SHC or variant genes and producing the wild type SHC or variant enzymes is termed a biocatalyst which is suitable for use in a bioconversion reaction. In some embodiments the biocatalyst is a recombinant whole cell producing wild type SHC or variant enzymes or it may be in suspension or an immobilized format.

In one embodiment, the biocatalyst is produced in sufficient amounts (to create a sufficient biomass), harvested and washed (and optionally stored (e.g. frozen or lyophilized)) before the bioconversion step.

In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process while reducing costs. The culture medium used to grow the cells is also suitable for use in the bioconversion reaction provided that the reaction conditions are adjusted to facilitate the bioconversion reaction.

The bioconversion methods of the present disclosure are carried out under conditions of time, temperature, pH and solubilizing agent to provide for conversion of the homofarnesol feedstock to (−)-Ambrox The pH of the reaction mixture may be in the range of 4-8, preferably, 5 to 6.5, more preferably 4.8-6.0 for the SHC variant enzymes and in the range of from about pH 5.0 to about pH 7.0 for the wild type SHC enzyme and can be maintained by the addition of buffers to the reaction mixture. An exemplary buffer for this purpose is a citric acid buffer. The preferred temperature is between from about 15° C. and about 45° C., preferably about 20° C. and about 40° C. although it can be higher, up to 55° C. for thermophilic organisms especially if the wild type enzyme from a thermophilic microorganism is used. The temperature can be kept constant or can be altered during the bioconversion process.

The Applicant has demonstrated that it may be useful to include a solubilizing agent (e.g. a surfactant, detergent, solubility enhancer, water miscible organic solvent and the like) in the bioconversion reaction. Examples of surfactants include but are not limited to Triton X-100, Tween 80, taurodeoxycholate, Sodium taurodeoxycholate, Sodium dodecyl sulfate (SDS), and/or sodium lauryl sulfate (SLS).

The Applicant has selected and identified SDS as a particularly useful solubilizing agent from a long list of other less useful solubilizing agents. In particular, the Applicant identified SDS as a remarkably better solubilizing agent than e.g. Triton X-100 in terms of reaction velocity and yield for the homofarnesol to (−)-Ambrox bioconversion reaction.

Without wishing to be bound by theory, the use of SDS with recombinant microbial host cells may be advantageous as the SDS may interact advantageously with the host cell membrane in order to make the SHC enzyme (which is a membrane bound enzyme) more accessible to the homofarnesol substrate. In addition, the inclusion of SDS at a suitable level in the reaction mixture may improve the properties of the emulsion (homofarnesol in water) and/or improve the access of the homofarnesol substrate to the SHC enzyme within the host cell while at the same time preventing the disruption (e.g. denaturation/inactivation of the wild type SHC or variant enzyme).

The concentration of the solubilising agent (e.g. SDS) used in the bioconversion reaction is influenced by the biomass amount and the substrate (EEH) concentration. That is, there is a degree of interdependency between the solubilising agent (e.g. SDS) concentration, the biomass amount and the substrate (EEH) concentration. By way of example, as the concentration of homofarnesol substrate increases, sufficient amounts of biocatalyst and solubilising agent (e.g. SDS) are required for an efficient bioconversion reaction to take place. If, for example, the solubilising agent (e.g. SDS) concentration is too low, a suboptimal homofarnesol conversion may be observed. On the other hand, if, for example, the solubilising agent (e.g. SDS) concentration is too high, then there may be a risk that the biocatalyst is affected through either the disruption of the intact microbial cell and/or an denaturation/inactivation of the SHC/HAC enzyme.

The selection of a suitable concentration of SDS in the context of the biomass amount and substrate (EEH) concentration is within the knowledge of the Skilled Person. By way of example, a predictive model is available to the Skilled Person to determine the suitable SDS, substrate (EEH) and biomass concentrations.

The temperature of the bioconversion reaction for a wild type SHC enzyme is from about 45-60° C., preferably 55° C.

The pH range of the bioconversion reaction for a wild type SHC enzyme is from about 5.0 to 7.0, more preferably from about 5.6 to about 6.2, even more preferably about 6.0.

The temperature of the bioconversion reaction for a SHC variant enzyme is about 34° C. to about 50° C., preferably about 35° C.

The pH of the bioconversion reaction for a SHC variant enzyme is about 4.8-6.4, preferably about 5.2-6.0.

Preferably the solubilising agent used in the bioconversion reaction is SDS.

The [SDS]/[cells] ratio is in the range of about, 10:1-20:1, preferably about 15:1-18:1, preferably about 16:1 when the ratio of biocatalyst to EEH homofarnesol is about 2:1

The SDS concentration in the bioconversion reaction for a SHC variant enzyme is in the range of about 1-2%, preferably in the range of about 1.4-1.7%, even more preferably about 1.5% when the homofarnesol concentration is about 125 g/l EEH and the biocatalyst concentration is 250 g/l (corresponding to an OD of about 175 (650 nm)).

The ratio of biocatalyst to EEH homofarnesol substrate is in the range of about 0.5:1-2:1, in some embodiments 2:1, preferably about 1:1 or 0.5:1.

In some embodiments, (−)-Ambrox is produced using a biocatalyst to which the homofarnesol substrate is added. It is possible to add the substrate by feeding using known means (e.g. peristaltic pump, infusion syringe and the like). Homofarnesol is an oil soluble compound and is provided in an oil format. Given that the biocatalyst is present in an aqueous phase, the bioconversion reaction may be regarded as a two phase system when homofarnesol is added to the bioconversion reaction mixture. This is the case even when a solubilizing agent (e.g. SDS) is present.

Further details of a suitable bioconversion process are disclosed in the examples, set forth herein below.

The bioconversion process according to the present invention produces a reaction mixture containing the desired (−)-Ambrox, and also a number of by-products. More particularly, the reaction mixture contains, in addition to (−)-Ambrox a complex mixture of by-products, including a novel constitutional isomer of (−)-Ambrox according to the formula (II), as well as known stereo isomers of (−)-Ambrox according to the formulae (III) and (IV)

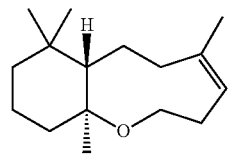

(II)

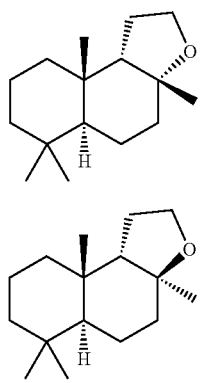

The applicant believes, although does not intend to be bound by any particular theory, that the compound of formula (II) is formed by the cyclization of the 7E,3Z-geometric isomer of homofarnesol. It has been described as practically odourless, with a detection threshold of >500 ng/l.

As stated above, the applicant believes that the compound of formula (II) is a novel molecule, and as such, this compound forms a further aspect of the present invention. Perfume ingredients and perfume compositions consisting of or comprising the compound (II), as well as perfumed articles containing same, form additional aspects of the invention.

The use of the compound of formula (II) as a perfume ingredient in perfumery applications, such as fine perfumes or functional perfume compositions such as personal care, household care and fabric care compositions, forms further additional aspects of the invention.

Mixtures of (−)-Ambrox and an olfactory acceptable amount of compound (II) forms still another aspect of the present invention.

The term "olfactory acceptable amount" as used herein in relation to the compound of formula (II), or any of the other by-products (III) or (IV), or indeed, any material that may be present as an impurity in (−)-Ambrox formed in accordance with a method of the present invention, is understood to mean that the compound or material is present in a mixture with (−)-Ambrox in an amount below its odour detection threshold, or in an amount at which it will not contribute its olfactory characteristics in a way that will affect the olfactory character of (−)-Ambrox. (−)-Ambrox containing an olfactory acceptable amount of any such compound or material would be identifiable to a skilled perfumer as possessing the odour character of commercial grades of (−)-Ambrox, such as AMBROFIX™ obtained by a synthetic procedure ex-sclareol, and available from Givaudan.

In preferred embodiments of the present invention, the reaction mixture contains no, or substantially no, unreacted homofarnesol.

The applicant discovered that homofarnesol was a powerful solvent for (−)-Ambrox as well as for the aforementioned by-products of the bioconversion process. As such, in the presence of appreciable amounts of homofarnesol, (−)-Ambrox and the by-products remain dissolved together in a crude, intractable mixture, from which it is difficult, protracted and costly to separate and ultimately isolate (−)-Ambrox in olfactively pure form. Reducing the level of unreacted homofarnesol in admixture with (−)-Ambrox and the compounds (II), (III) and (IV) was found to considerably facilitate downstream processing and isolation/purification of (−)-Ambrox.

Downstream processing, as will be appreciated by persons skilled in the art, is a critical operation in the manufacture of useful compounds formed by bioconversion processes. As part of the synthesis of a compound, it can affect the compound's physical properties. In the case of the preparation of perfume ingredients by biotech methods, it is desirable that a target compound can be separated from a reaction mixture in olfactively pure form in order that the desired odour characteristics of the target compound are not distorted by odour contributions of the complex mixture of contaminants and by-products that may be present in the fermentation medium or the biocatalyst.

Accordingly, the invention provides in another of its aspects a method of isolating and purifying (−)-Ambrox from a reaction mixture, comprising one or more of the compounds (II), (III) and (IV).

In yet another aspect of the present invention there is provided a method of improving or enhancing the odour of (−)-Ambrox, comprising the steps of separation and purification of (−)-Ambrox from a reaction mixture containing one or more of the compounds (II), (III) and (IV).

In an isolated and purified form, (−)-Ambrox either does not contain any of the compounds (II), (III) or (IV), or if it does contain any of said compounds, then each should be present in an olfactory acceptable amount.

The reaction mixture obtained from the bioconversion process, such as a process as described herein above, generally comprises a solid phase containing crude (−)-Ambrox and one or more of the by-products (II), (III) and (IV), as well as cellular material and/or debris thereof; and a liquid phase or liquid phases comprising water and/or any unreacted homofarnesol.

The solid phase may be separated from the liquid phase or phases by filtration or centrifugation. Furthermore, by selecting a filter with an appropriate pore size, it is also possible to effect separation of the crude (−)-Ambrox, from the cellular material and/or debris. Once the crude (−)-Ambrox is separated from cellular material and/or debris thereof, it may be washed, before being subjected to further work-up procedures to isolate (−)-Ambrox from compounds (II), (III) and (IV).

Alternatively, instead of filtration or centrifugation, the reaction mixture can be warmed to a temperature above the melting point of (−)-Ambrox, whereupon (−)-Ambrox forms an oil phase above an aqueous phase containing the cellular material and debris. Optionally, and in order to ensure a complete recovery of (−)-Ambrox, the aqueous and cellular material can be washed with a water-immiscible organic solvent (such as toluene) to remove any residual (−)-Ambrox that may have been entrained in the aqueous phase, and these washings can be combined with the oil phase. The oil phase can thereafter be concentrated by evaporation to provide a crude mixture comprising (−)-Ambrox and one or more of the compounds (II), (III) and (IV),which mixture can then subjected to further work-up procedures to isolate and purify (−)-Ambrox.

In another embodiment, instead of warming the reaction mixture to form a (−)-Ambrox-containing oil phase, the reaction mixture can be extracted with a suitable water-immiscible organic solvent (such as toluene) to form an organic phase containing (−)-Ambrox and one or more of the compounds (II), (III) and (IV), which can be separated from an aqueous phase containing the cellular material and debris. The organic phase can be concentrated by evaporation to provide a crude mixture comprising (−)-Ambrox and one or more of the compounds (II), (III) and (IV), which can be subjected to further work-up procedures to isolate and purify (−)-Ambrox.

In yet another alternative method, the reaction mixture can be steam distilled to remove the distillate from the cellular material and debris. The distillate can be collected as a biphasic mixture, before the oil phase of the biphasic mixture comprising a mixture of (−)-Ambrox and one or more of the compounds (II), (III) and (IV) is separated from the aqueous phase, and then subjected to further work-up procedures to isolate and purify (−)-Ambrox.

In a particular embodiment of the present invention, said method of isolating and purifying (−)-Ambrox comprises the step of selectively crystallizing (−)-Ambrox from a mixture containing one or more of the compounds (II), (III) or (IV).

The phrase "selectively crystallizing" refers to a process step whereby (−)-Ambrox is caused to crystallize from a solvent, whilst the compounds (II), (III) and (IV) remain dissolved in the crystallizing solvent, to such an extent that isolated crystalline material contains only (−)-Ambrox, or if it contains any of the compounds (II), (III) or (IV), then they are present only in olfactory acceptable amounts.

Crystallization may be carried out in a suitable organic solvent. The choice of solvent is based on considerations, such as solubility differences at room temperature and at high temperatures, or in boiling solvent; and for the need of an abundance of crystals recoverable in cool solvent. Usually, a compound to be separated is dissolved in a relatively polar solvent and then a relatively less polar solvent can be added to bring the dissolved compound to its solubility limit, whereupon it will start to crystallize. Also, in an industrial process, issues of cost as well as safety of handling are relevant. Suitable solvents include, but are not limited to methanol, acetone, petroleum ether, hexane, t-butyl methyl ether, THF and ethyl acetate. Preferred solvents include toluene or ethyl alcohol. Pairs of solvents may also be employed.

In a particularly preferred embodiment of the present invention, selective crystallization is undertaken by dissolving the mixture containing (−)-Ambrox and one or more of the compounds (II), (III) and (IV) in warm ethanol and allowing (−)-Ambrox to selectively crystallize by slowly adding a non-solvent, such as water, to the cooling ethanolic solution.

Considering the close structural relationship of (−)-Ambrox and the by-product compounds (II), (III) and (IV), which are respectively a constitutional isomer and two stereoisomers of (−)-Ambrox, it was remarkable that (−)-Ambrox could be selectively crystallized from such a mixture, to provide (−)-Ambrox in olfactively pure form and in high yields. The skilled person would reasonably anticipate that the compounds would co-crystallize with (−)-Ambrox, rendering downstream processing far more complex, time-consuming and expensive than was found to be the case.

The surprisingly facile manner in which (−)-Ambrox could be separated from a mixture containing compound (II), (III) and/or (IV) by crystallization represents a particular advantage of the present invention.

The ease with which (−)-Ambrox could be separated by crystallization could be contrasted with the observation that (−)-Ambrox could not be recovered in such a facile manner and in such high yield from a mixture containing (II), (III) and/or (IV) by other purification techniques, such as by distillation, owing to the very similar boiling points of (−)-Ambrox and the by-products (II), (III) and (IV).

The term "olfactively pure" as it is used in relation to (−)-Ambrox, is intended to mean that (−)-Ambrox is free of compounds (II), (III) or (IV), or any other material found in the reaction mixture, or that if such compounds or materials should be present, they are present in olfactory acceptable amounts, as that term is defined herein.

In an embodiment of the invention (−)-Ambrox in olfactively pure form contains less than 5% by weight of any of the compounds (II), (III) or (IV).

In more particular embodiments, (−)-Ambrox in olfactively pure form contains less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, or less than 0.05% by weight of each of the compounds (II), (III) or (IV).

The quality of separation of (−)-Ambrox from the mixture of the compounds (II), (III) and/or (IV) by selective crystallization may be influenced by the composition of the mixture from which it is separated. More particularly, the quality of the separation of (−)-Ambrox from a mixture of compounds (II), (III) and/or (IV) by crystallization was improved when the weight ratio of (−)-Ambrox to the other compounds (II), (III) and (IV) in the mixture was greater than 70:30, more particularly 80:20, more particularly 90:10, still more particularly 95:5, and more particularly still 97:3.

Furthermore, the quality of the separation of (−)-Ambrox by crystallization may be influenced by the amount of unreacted homofarnesol present in the mixture from which it is separated. More particularly, the quality of separation is improved when the level of unreacted homofarnesol is less than 30 wt % by weight, more particularly less than 20 wt %, more particularly less than 10% by weight, more particularly still less than 5 wt % and still more particularly less than 3% by weight, still more particularly less than 2% by weight, and more particularly still less than 1% by weight, based on the weight of the mixture from which (−)-Ambrox is crystallized.

Preferably, the reagents and reaction conditions employed in the bioconversion process of the present invention are such that the reaction proceeds with 100% conversion of homofarnesol, or substantially so, thus leaving no unreacted homofarnesol in the reaction mixture. However, if unreacted homofarnesol is present, although economically disadvantageous, it can be separated from (−)-Ambrox and other by-products by distillation, for example.

Accordingly, in a particular embodiment of the invention, there is provided a method of isolating and purifying (−)-Ambrox from a mixture comprising one or more of the compounds (II), (III) and (IV), which mixture is free, or substantially free, of homofarnesol.

In a more particular embodiment, the isolation and purification of (−)-Ambrox from a mixture comprising one or more of the compounds (II), (III) and (IV), and free or substantially free of homofarnesol, is achieved by the selective crystallization of (−)-Ambrox.

(−)-Ambrox obtained according to a method of the present invention is obtained in olfactively pure form. Olfactively pure (−)-Ambrox forms another aspect of the present invention.

(−)-Ambrox in crystalline form forms yet another aspect of the present invention.

(−)-Ambrox formed in accordance with the method of the present invention may be mixed with one or more additional perfume ingredients to form perfume compositions that find use in perfumery applications, including use in fine perfumery, as well as use in consumer products, such as personal care, fabric care and household care applications.

Accordingly, the invention provides in another of its aspects a perfume composition comprising (−)-Ambrox and at least one other perfume ingredient, wherein said perfume composition contains olfactory acceptable amounts of one or more of the compounds (II), (III) or (IV).

The invention will be further illustrated with reference to the following examples.

EXAMPLES

Example 1

Preparation of Homofarnesol
General Analytical Conditions:

Non-polar GC/MS: 50° C./2 min, 20° C./min 200° C., 35° C./min 270° C. GC/MS Agilent 5975C MSD with HP 7890A Series GC system. Non-polar column: BPX5 from SGE, 5% phenyl 95% dimethylpolysiloxane 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

A) Preparation of MNU in THF

A solution of urea (175 g, 2.9 mol) and methylamine hydrochloride (198 g, 2.9 mol) in water (400 ml) is heated at reflux (105° C.) for 3.5 h under stirring. At 40° C. NaNO2 (101 g, 1.45 mol) dissolved in water (200 ml) is added. After 15 min THF (1000 ml) is added which results in a transparent 2-phase mixture. Conc. H2SO4 (110 g, 1.1 mol) is added at 0-5° C. and stirring within 1.5 h. After another 0.5 h at 0-5° C. the two transparent phases are separated at 25° C. The organic phase (A) (1065 ml, theoretically 1.35 M) is stored for a few days at 0-5° C. or forwarded immediately to the cyclopropanation reactor.

After phase separation the water phase is extracted twice with THF (2×1 l). This gives 1100 ml of phase B and 1075 of phase C. Whereas phase A gives a 51% conversion of a terminal alkene to a cyclopropane in a subsequent cyclopropanation reaction, phase B gives <0.5% cyclopropane and phase C gives no detectable conversion. We conclude that >99% MNU is extracted after the first phase separation. Usually the water phase is therefore discarded after the first phase separation (from organic phase A) after treatment with conc. aqueous KOH and acetic acid.

B) Preparation of E-Δ-Farnesene Using MNU in THF

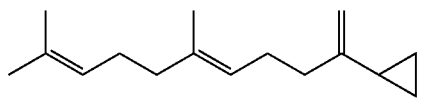 [SMILES: C=C(CC/C=C(\C)CCC=C(C)C)C1CC1]

N-Methyl-N-nitroso urea 1.35 M in THF (136 ml, 184 mmol) is added dropwise at 0° C. to a rapidly stirred mixture of E-beta-Farnesene (CAS 18794-84-8) (25 g, 122 mmol) and aqueous KOH (50 ml, 40%) at 0-5° C. After the addition of 4 ml of the MNU solution, Pd(acac)2 (7.4 mg, 0.024 mmol, 0.02%) pre-dissolved in 0.5 ml dichloromethane is added. The remaining MNU solution is added over 4 h at 0-5° C. A GC at this stage showed 28% unconverted E-beta-Farnesene, 65% of the desired monocyclopropane (shown above) and 3% of a biscyclopropanated compound 5. After 16 h at 25° C. acetic acid (100 ml) is added at 0-5° C., then tert-butyl methyl ether (250 ml). After phase separation the organic phase is washed with 2M HCl (250 ml) and the aqueous phase extracted with tert-butyl methyl ether (250 ml). The combined organic layers are washed with water (2×100 ml), aqueous 10% NaOH (2×100 ml) and water (2×100 ml), dried over MgSO4, filtered and concentrated to give 26.9 g of a slightly yellow liquid which contains 9% E-beta-Farnesene, 82% of the desired monocyclopropane compound and 6% of a biscyclopropanated side product.

The desired compound could be further isolated by distillative purification.

Addition of 1 g K2CO3 (1 g) and distillation over a 30 cm steel coil column at 40-60 mbar gives 147 g monocyclopropane compound (68% corr) at 135-145° C. The fractions are pooled to give 92 g monocyclopropane compound of 100% purity.

Analytical data of E-Δ Farnesene:

1H-NMR (CDCl3, 400 MHz): 5.1 (2 m, 2 H), 4.6 (2 H), 2.2 (2 H), 2.1 (4 H), 2.0 (2 H), 1.7 (s, 3 H), 1.6 (2 s, 6 H), 1.3 (1 H), 0.6 (2 H), 0.45 (2 H) ppm. 13C-NMR (CDCl3, 400 MHz): 150.9 (s), 135.1 (s), 131.2 (s), 124.4 (d), 124.1 (d), 106.0 (t), 39.7 (t), 35.9 (t), 26.7 (t), 25.7 (q), 17.7 (q), 16.0 (d), 6.0 (t) ppm. GC/MS: 218 (2%, M+), 203 (5%, [M−15]+), 175 (11%), 147 (31%), 134 (15%), 133 (20%), 121 (12%), 107 (55%), 95 (16%), 93 (30%), 91 (20%), 82 (11%), 81 (33%), 79 (42%), 69 (100%), 67 (22%), 55 (20%), 53 (21%), 41 (75%). IR (film): 3081 (w), 2967 (m), 2915 (m), 2854 (m), 1642 (m), 1439 (m), 1377 (m), 1107 (w), 1047 (w), 1018 (m), 875 (s), 819 (m), 629 (w). Anal. calcd. for C16H26: C, 88.00; H, 12.00. Found: C, 87.80; H, 12.01.

C) Preparation of (7E)-4,8,12-trimethyltrideca-3,7,11-trien-1-ol ((7E)-homofarnesol)

A mixture of (E)-(6,10-dimethylundeca-1,5,9-trien-2-yl) cyclopropane (E-Δ Farnesene) (1 g, 4.6 mmol), dodecane (0.2 g, 1.15 mmol, internal standard) and L-(+)-tartaric acid (1 g, 6.9 mmol) in a pressure tube is heated under stirring at 150° C. After 18 h and complete conversion (according to GC) the mixture is poured on water (50 ml) and toluene (50 ml). The phases are separated and the aqueous phase extracted with toluene (50 ml). The combined organic layers are washed with conc. aqueous Na2CO3 (50 ml) and conc. NaCl (2×50 ml), dried over MgSO4, filtered and evaporated under reduced pressure to give a brownish resin (1.35 g) which is mixed with 30% aqueous KOH (4.3 ml) and stirred at 25° C. for 2 h. GC analysis reveals formation of 96% (7E)-4,8,12-trimethyltrideca-3,7,11-trien-1-ol according to the internal standard. E/Z ratio 68:22. The analytical data of the E-isomer are consistent with the ones from the literature, see for example P. Kocienski, S. Wadman J. Org. Chem. 54, 1215 (1989).

Example 2

SHC Plasmid Preparation and Biocatalyst Production
SHC Plasmid Preparation

The gene encoding *Alicyclobacillus acidocaldarius* squalene hopene cyclase (AacSHC) (GenBank M73834, Swissprot P33247) was inserted into plasmid pET-28a(+), where it is under the control of an IPTG inducible T7-promotor for protein production in *Escherichia coli*. The plasmid was transformed into *E. coli* strain BL21(DE3) using a standard heat-shock transformation protocol.

Erlenmeyer Flask Cultures

For protein production were used either rich medium (LB medium) or minimal media. M9 is one example of minimal media, which were successfully used.

Media Preparation

The minimal medium chosen as default was prepared as follows for 350 ml culture: to 35 ml citric acid/phosphate stock (133 g/l $KH_2PO_4$, 40 g/l $(NH_4)_2HPO_4$, 17 g/g citric acid.$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (composition in next section) solution, 0.035 ml Thiamin solution and 7 ml 20% glucose were added.

SHC Biocatalyst Production (Biocatalyst Production)

Small scale biocatalyst production (wild-type SHC or SHC variants), 350 ml culture (medium supplemented with 50 µg/ml kanamycin) were inoculated from a pre-culture of the *E. coli* strain BL21(DE3) containing the SHC production plasmid. Cells were grown to an optical density of approximately 0.5 ($OD_{650\,nm}$) at 37° C. with constant agitation (250 rpm).

Protein production was then induced by the addition of IPTG to a concentration of 300 µM followed by incubation for a further 5-6 hours with constant shaking. The resulting biomass was finally collected by centrifugation, washed with 50 mM Tris-HCl buffer pH 7.5. The cells were stored as pellets at 4° C. or −20° C. until further use. In general 2.5 to 4 grams of cells (wet weight) were obtained from 1 litre of culture, independently of the medium used.

The fermentation was prepared and run in 750 ml InforsHT reactors. To the fermentation vessel was added 168 ml deionized water. The reaction vessel was equipped with all required probes ($pO_2$, pH, sampling, antifoam), C+N feed and sodium hydroxide bottles and autoclaved. After autoclaving, the following ingredients are added to the reactor:

20 ml 10× phosphate/citric acid buffer
14 ml 50% glucose
0.53 ml $MgSO_4$ solution
2 ml $(NH_4)_2SO_4$ solution
0.020 ml trace elements solution
0.400 ml thiamine solution
0.200 ml kanamycin stock The reaction conditions are set as follows: pH=6.95, $pO_2$=40%, T=30° C., Stirring at 300 rpm. Cascade: rpm setpoint at 300, min 300, max 1000, flow l/min set point 0.1, min 0, max 0.6. Antifoam control: 1:9.

The fermenter was inoculated from a seed culture to an $OD_{650\,nm}$ of 0.4-0.5. This seed culture was grown in LB medium (+Kanamycin) at 37° C., 220 rpm for 8 h. The fermentation was run first in batch mode for 11.5 h, where after was started the C+ N feed with a feed solution (sterilized glucose solution (143 ml $H_2O$+ 35 g glucose) to which had been added after sterilization: 17.5 ml $(NH_4)_2SO_4$ solution, 1.8 ml $MgSO_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approximately 25 hours, where they reached typically and $OD_{650\,nm}$ of 40-45. SHC production was then started by adding IPTG to a final concentration of approx. 1 mM in the fermenter (as IPTG pulse or over a period of 3-4 hours using an infusion syringe), setting the temperature to 40° C. and $pO_2$ to 20%. Induction of SHC production lasted for 16 h at 40° C. At the end of induction the cells were collected by centrifugation, washed with 0.1 M citric acid/sodium citrate buffer pH 5.4 and stored as pellets at 4° C. or −20° C. until further use.

Results Ia

In general, with all other conditions unchanged the specific activity of the produced biocatalyst was higher when a minimal medium was used compared with a rich medium.

Induction was carried out successfully at 30 or 37° C. It was noted that when the induction was done at 40-43° C., a biocatalyst of higher specific activity was obtained.

Results Ib

The following Table 1 shows for two examples the culture volume, optical density and amount of cells both at induction start and induction end as well as the amount of biomass collected (wet weight).

TABLE 1

|  | $Volume_{induction\,start}$ (ml) | $OD_{650\,nm\,induction\,start}$ | cells calculated (g) | $Volume_{induction\,end}$ (ml) | $OD_{650\,nm,\,induction\,end}$ | cells collected (g) |
| --- | --- | --- | --- | --- | --- | --- |
| Example 1 | 273 | 40 | 10.9 | 342 | 55 | 28 |
| Example 2 | 272 | 44 | 12.0 | 341 | 57 | 23 |

$OD_{650\,nm}$ at inoculation: 0.45 (Example 1) and 0.40 (Example 2). Starting volumes: 205 ml.

```
Wild type SHC amino acid sequence (SEQ ID No. 1) (GenBank M73834, Swissprot P33247)
MAEQLVEAPAYARTLDRAVEYLLSCQKDEGYWWGPLLSNVTMEAEYVLLCHILDRVDRDRMEKIRRYLLHEQREDGTWALY PGGPPDLDTTIEAYVALKYIGMSRDEEPMQKALRFIQSQGGIESSRVFTRMWLALVGEYPWEKVPMVPPEIMFLGKRMPLN IYEFGSWARATVVALSIVMSRQPVFPLPERARVPELYETDVPPRRRGAKGGGGWIFDALDRALHGYQKLSVHPFRRAAEIR ALDWLLERQAGDGSWGGIQPPWFYALTALKILDMTQHPAFIKGWEGLELYGVELDYGGWMFQASISPVWDTGLAVLALRAA GLPADHDRLVKAGEWLLDRQITVPGDWAVKRPNLKPGGFAFQFDNVYYPDVDDTAVVVWALNTLRLPDERRRRDAMTKGFR WIVGMQSSNGGWGAYDVDNTSDLPNHIPFCDFGEVTDPPSEDVTAHVLECFGSFGYDDAWKVIRRAVEYLKREQKPDGSWF GRWGVNYLYGTGAVVSALKAVGIDTREPYIQKALDWVEQHQNPDGGWGEDCRSYEDPAYAGKGASTPSQTAWALMALIAGG

RAESEAARRGVQYLVETQRPDGGWDEPYYTGTGFPGDFYLGYTMYRHVFPTLALGRYKQAIERR
```

-continued

Variant F601Y SHC amino acid sequence (SEQ ID No. 2)-variant with respect to
SEQ ID No. 1
MAEQLVEAPAYARTLDRAVEYLLSCQKDEGYWWGPLLSNVTMEAEYVLLCHILDRVDRDRMEKIRRYLLHEQREDGTWALY PGGPPDLDTTIEAYVALKYIGMSRDEEPMQKALRFIQSQGGIESSRVFTRMWLALVGEYPWEKVPMVPPEIMFLGKRMPLN IYEFGSWARATVVALSIVMSRQPVFPLPERARVPELYETDVPPRRRGAKGGGGWIFDALDRALHGYQKLSVHPFRRAAEIR ALDWLLERQAGDGSWGGIQPPWFYALTALKILDMTQHPAFIKGWEGLELYGVELDYGGWMFQASISPVWDTGLAVLALRAA GLPADHDRLVKAGEWLLDRQITVPGDWAVKRPNLKPGGFAFQFDNVYYPDVDDTAVVVWALNTLRLPDERRRRDAMTKGFR WIVGMQSSNGGWGAYDVDNTSDLPNHIPFCDFGEVTDPPSEDVTAHVLECFGSFGYDDAWKVIRRAVEYLKREQKPDGSWF GRWGVNYLYGTGAVVSALKAVGIDTREPYIQKALDWVEQHQNPDGGWGEDCRSYEDPAYAGKGASTPSQTAWALMALIAGG

RAESEAARRGVQYLVETQRPDGGWDEPYYTGTGYPGDFYLGYTMYRHVFPTLALGRYKQAIERR

Variant F605W SHC nucleotide sequence (SEQ ID No. 3)
ATGGCTGAGCAGTTGGTGGAAGCGCCGGCCTACGCGCGGACGCTGGATCGCGCGGTGGAGTATCTCCTCTCCTGCCAAAAG GACGAAGGCTACTGGTGGGGGCCGCTTCTGAGCAACGTCACGATGGAAGCGGAGTACGTCCTCTTGTGCCACATTCTCGAT CGCGTCGATCGGGATCGCATGGAGAAGATCCGGCGGTACCTGTTGCACGAGCAGCGCGAGGACGGCACGTGGGCCCTGTAC CCGGGTGGGCCGCCGGACCTCGACACGACCATCGAGGCGTACGTCGCGCTCAAGTATATCGGCATGTCGCGCGACGAGGAG CCGATGCAGAAGGCGCTCCGGTTCATTCAGAGCCAGGGCGGGATCGAGTCGTCGCGCGTGTTCACGCGGATGTGGCTGGCG CTGGTGGGAGAATATCCGTGGGAGAAGGTGCCCATGGTCCCGCCGGAGATCATGTTCCTCGGCAAGCGCATGCCGCTCAAC ATCTACGAGTTTGGCTCGTGGGCTCGGGCGACCGTCGTGGCGCTCTCGATTGTGATGAGCCGCCAGCCGGTGTTCCCGCTG

CCCGAGCGGGCGCGCGTGCCCGAGCTGTACGAGACCGACGTGCCTCCGCGCCGGCGCGGTGCCAAGGGAGGGGTGGGTGG

ATCTTCGACGCGCTCGACCGGGCGCTGCACGGGTATCAGAAGCTGTCGGTGCACCCGTTCCGCCGCGCGGCCGAGATCCGC

GCCTTGGACTGGTTGCTCGAGCGCCAGGCCGGAGACGGCAGCTGGGGCGGGATTCAGCCGCCTTGGTTTTACGCGCTCATC

GCGCTCAAGATTCTCGACATGACGCAGCATCCGGCGTTCATCAAGGGCTGGGAAGGTCTAGAGCTGTACGGCGTGGAGCTG

GATTACGGAGGATGGATGTTTCAGGCTTCCATCTCGCCGGTGTGGGACACGGGCCTCGCCGTGCTCGCGCTGCGCGCTGCG

GGGCTTCCGGCCGATCACGACCGCTTGGTCAAGGCGGGCGAGTGGCTGTTGGACCGGCAGATCACGGTTCCGGGCGACTGG

GCGGTGAAGCGCCCGAACCTCAAGCCGGGCGGGTTCGCGTTCCAGTTCGACAACGTGTACTACCCGGACGTGGACGACACG

GCCGTCGTGGTGTGGGCGCTCAACACCCTGCGCTTGCCGGACGAGCGCCGCAGGCGGGACGCCATGACGAAGGGATTCCGC

TGGATTGTCGGCATGCAGAGCTCGAACGGCGGTTGGGGCGCCTACGACGTCGACAACACGAGCGATCTCCCGAACCACATC

CCGTTCTGCGACTTCGGCGAAGTGACCGATCCGCCGTCGAGGACGTCACCGCCCACGTGCTCGAGTGTTTCGGCAGCTTC

GGGTACGATGACGCCTGGAAGGTCATCCGGCGCGCGGTGGAATATCTCAAGCGGGAGCAGAAGCCGGACGGCAGCTGGTTC

GGTCGTTGGGGCGTCAATTACCTCTACGGCACGGGCGCGGTGGTGTCGGCGCTGAAGGCGGTCGGGATCGACACGCGCGAG

CCGTACATTCAAAAGGCGCTCGACTGGGTCGAGCAGCATCAGAACCCGGACGGCGGCTGGGGCGAGGACTGCCGCTCGTAC

GAGGATCCGGCGTACGCGGGTAAGGGCGCGAGCACCCCGTCGCAGACGGCCTGGGCGCTGATGGCGCTCATCGCGGGCGGC

AGGGCGGAGTCCGAGGCCGCGCGCCGCGGCGTGCAATACCTCGTGGAGACGCAGCGCCCGGACGGCGGCTGGGATGAGCCG

TACTACACCGGCACGGGCTTCCCAGGGGATTGGTACCTCGGCTACACCATGTACCGCCACGTGTTTCCGACGCTCGCGCTC

GGCCGCTACAAGCAAGCCATCGAGCGCAGGTGA

Variant F605W SHC amino acid sequence (SEQ ID No. 4)-variant with respect to
SEQ ID No. 1
MAEQLVEAPAYARTLDRAVEYLLSCQKDEGYWWGPLLSNVTMEAEYVLLCHILDRVDRDRMEKIRRYLLHEQREDGTWALY PGGPPDLDTTIEAYVALKYIGMSRDEEPMQKALRFIQSQGGIESSRVFTRMWLALVGEYPWEKVPMVPPEIMFLGKRMPLN IYEFGSWARATVVALSIVMSRQPVFPLPERARVPELYETDVPPRRRGAKGGGGWIFDALDRALHGYQKLSVHPFRRAAEIR ALDWLLERQAGDGSWGGIQPPWFYALTALKILDMTQHPAFIKGWEGLELYGVELDYGGWMFQASISPVWDTGLAVLALRAA GLPADHDRLVKAGEWLLDRQITVPGDWAVKRPNLKPGGFAFQFDNVYYPDVDDTAVVVWALNTLRLPDERRRRDAMTKGFR WIVGMQSSNGGWGAYDVDNTSDLPNHIPFCDFGEVTDPPSEDVTAHVLECFGSFGYDDAWKVIRRAVEYLKREQKPDGSWF GRWGVNYLYGTGAVVSALKAVGIDTREPYIQKALDWVEQHQNPDGGWGEDCRSYEDPAYAGKGASTPSQTAWALMALIAGG

RAESEAARRGVQYLVETQRPDGGWDEPYYTGTGFPGDWYLGYTMYRHVFPTLALGRYKQAIERR

Example 3

Bioconversion of 7E, 3E/Z-Homofarnesol Mixture

Bioconversion was undertaken using the following reaction conditions:

The reaction (150.1 g total volume) run in 0.1 M citric acid/sodium citrate buffer pH 5.4 in an InforsHT 750 ml fermenter contained 146 g/l total homofarnesol using a homofarnesol substrate, which was a mixture of 7E,3E:7E, 3Z of 86:14, 250 g/l cells (formed in accordance with the method of Example 2, fermentation) and 1.55% SDS. The reaction was run at 35° C. with constant stirring (900 rpm), pH control was done using 10 to 40% citric acid in water.

The reaction mixture was subjected to isolation and purification steps as set forth in Example 4, below.

Example 4

Downstream Processing Procedure

A reaction mixture formed from the bioconversion of 7E, 3E/Z-homofarnesol (86:14 3E:3Z) was subjected to steam distillation. The distillate was collected as a biphasic mixture. The organic phase was retained and the aqueous phase discarded. The composition of the organic phase was analysed by GC and the results shown in the Table 2 below (see "crude").

The organic phase was then concentrated to dryness. Ethanol was then added to the crude, dried product and the mixture warmed until the product was dissolved. At room temperature water is slowly added and (−)-Ambrox crystallizes under occasional stirring and cooling in an ice bath.

Table 1 shows the GC analytics results for the crystallized product. The data show a strong enrichment of (−)-Ambrox, with practically no by-products (a), (b) or (c) being found in the crystallized sample.

It should be noted that in Table 2, "a", "b" and "c" refer to compound (II), compound (IV) and compound (III) respectively. "EZH" and "EEH" refer to 7E,3Z-homofarnesol and 7E,3E-homofarnesol respectively.

chromatography) of the aqueous phase after MTBE extraction showed that it contained not more than approx. 0.3% of the (−)-Ambrox initially present in the 200 ml reaction broth. Toluene and ethanol 99% were used for extracting (−)-Ambrox from the solid phase.

Toluene Extraction:

80 ml solid phase was extracted 6× with 45 ml toluene (approx. ½ solid phase volume, vigorous shaking for 30 s, centrifugation (Sorvall GS3, 5000 rpm, 10 min, 10° C.). The solvent phase was analyzed with GC for its (−)-Ambrox content. Over 99.5% of (−)-Ambrox initially present in the reaction broth was extracted with 6 extractions representing a total toluene vol. of 1.35× the initial whole reaction broth volume (200 ml) or 3.4× the vol. of the solid phase.

Ethanol Extraction:

80 ml solid phase was extracted (Infors Multifors HT, 35° C., 1000 rpm, 30 min) with approx. 160 ml (2 vol.) ethanol 99%, followed by centrifugation. (−)-Ambrox did not crystallize during the extraction procedure. After 4 washes (total 640 ml ethanol, i.e. 3.2× the initial whole reaction broth volume or 8× the volume of the solid phase), about 99% of (−)-Ambrox initially present in the reaction broth was recovered. Sufficient ethanol is required in the first extraction step to prevent (−)-Ambrox crystallization (solubility in ethanol). When only 1 or ½ vol of the solid phase was used in the first extraction step, a sticky paste was obtained, which was difficult to handle and (−)-Ambrox crystallized as needles on the pellet during centrifugation. Temperature appeared as not being the factor responsible for this crystallization (extraction and centrifugation tested at room temperature and approx. 35° C.-40° C.).

The (−)-Ambrox concentration in the ethanol phase as well as the ethanol/water ratio of the liquid phase (residual moisture of the solid phase) appeared to be responsible for crystal formation. It was however noted that it was possible to reduce the volume of ethanol to 1 vol of the solid phase.

As (−)-Ambrox is not in the liquid phase at room temperature, it separates with the biomass and can be extracted with an organic solvent (e.g. a water-miscible solvent (e.g. ethanol) or a water-immiscible solvent (e.g. toluene). The centrifugation step that separates the (−)-Ambrox into the solid phase of the reaction mixture is advantageous because

TABLE 1

| | Peak area (GC) | | | | | | (—)-Ambrox |
|---|---|---|---|---|---|---|---|
| | a | b | c | (—)-Ambrox | EZH | EEH | (%) |
| Crude | 215073 | 190376 | 588769 | 6751605 | 13429 | 14184 | 86.9 |
| Crystallized | 10088 | 8951 | 64625 | 9032941 | 0 | 0 | 99.1 |

Example 5

Extraction of the solid phase of the reaction broth:

Given that (−)-Ambrox is not soluble in water and is not liquid at temperatures below approx. 75° C., these properties were taken as possible advantages to extract the product from the solid phase of the biotransformation using either water-miscible solvents (e.g. ethanol) and water-immiscible solvents (e.g. toluene).

200 ml reaction broth was centrifuged to separate the solid from the liquid (aqueous) phase (Sorvall GS3, 5000 rpm, 10 min, 10° C.). This separated approx. 80 ml solid pellet from approx. an 120 ml liquid phase. Analysis (Gas it reduces the amount of solvent required to extract (−)-Ambrox.

Example 6

Sensory Analysis

Purpose: to carry out a sensory analysis of (−)-Ambrox and the compounds (II), (III) and (IV) formed in the crude material and in the crystallised material.

Biotransformation of E,E-homofarnesol results in (−)-Ambrox, and compound (IV).

Biotransformation of E,Z-homofarnesol results in the macrocyclic ether compound (II) and epi-Ambrox compound (III).

A crude mixture of (−)-Ambrox comprises the desired (−)-Ambrox, compound (II), (III) and (IV) present in an amount of 87.1 wt %, 2.8 wt %, 2.5 wt % and 7.6 wt % respectively.

When a crude mixture is selectively crystallised (lab scale), the crystallised material has the same components as the crude mixture, but they are present in an amount of 99.1 wt %, 0.1 wt %, 0.1 wt % and 0.7 wt % respectively.

The Sensory Analytical Results were as follows:

(−)-Ambrox: Odour Threshold 0.2 ng/l.

Compound (IV): weak, IsoE, woody, GC-detection threshold 5-10 ng.

Compound (II): "odorless" (GC-threshold >500 ng).

Compound (III): GC-threshol about 10× higher than (−)-Ambrox (circa 2 ng).

The sensory analysis of the 3 by-products (compounds II, III and IV) indicates a weaker odour than that from (−)-Ambrox. In fact, the epi-ambrox (Compound III) odor is about 10 fold weaker than (−)-Ambrox suggesting that it is essentially odorless.

Example 7

Ambrox Recovery by Steam Extraction

Resulting Purity of the Crude (Steam Extracted) and Crystallized (−)-Ambrox

The biotransformation of EE:EZ-homofarnesol 86:14 provided a reaction mixture that was steam extracted. The steam distillate was collected as a biphasic mixture. The organic phase was retained and the aqueous phase discarded. The composition of the organic phase was analysed by GC and the results shown in the Table below (see "crude"). The organic phase was then concentrated to dryness. Ethanol was then added to the crude, dried product and the mixture warmed until the product was dissolved. At room temperature water is slowly added and (−)-Ambrox crystallizes under occasional stirring and cooling in an ice bath.

The tabulated data also shows the GC analytics results for products obtained after the steam extraction/distillation step ("crude") and the crystallized product ((−)-Ambrox). The references in the Table to "EZH" and "EEH" refer to (3Z,7E)-homofarnesol and 7E,3E-homofarnesol respectively.

The tabulated data below indicates that the particular starting material (EEH:EZH 86:14) produces the desired end product (−)-Ambrox and a very specific mixture of by-products (II, IV and III) using the WT SHC enzyme or a SHC derivative. The data for the selective crystallization show a strong enrichment of (−) Ambrox, with practically no by-products (II), (IV) or (III) being found in the crystallized sample. Accordingly, this EE:EZ mixture provides an olfactively pure (−)-Ambrox product, which is selectively crystallised in a relatively straightforward and cost-effective matter.

TABLE shows the GC analytics results for the crystallized product.

| | Peak area (GC) | | | | | | Ambrox |
|---|---|---|---|---|---|---|---|
| | (II) | (IV) | (III) | Ambrox | EZH | EEH | (%) |
| Crude | 215073 | 190376 | 588769 | 6751605 | 13429 | 14184 | 86.9 |
| Crystallized | 10088 | 8951 | 64625 | 9032941 | 0 | 0 | 99.1 |

Steam extraction/filtration are environmentally friendly methods for isolating (−)-Ambrox because it offers a convenient solvent-free isolation of (−)-Ambrox with an associated inactivation of the biocatalyst.

The (−)-Ambrox produced using the bioconversion reaction may be extracted using solvent from the whole reaction mixture (e.g. using a water-immiscible solvent or by steam extraction/distillation or by filtration) or from the solid phase (e.g. using a water miscible solvent) using methods which are known to those skilled in the art.

The invention claimed is:

1. A method of isolating and purifying (−)-Ambrox comprising the step of selectively crystallizing (−)-Ambrox from a reaction mixture comprising one or more of the compounds (II), (III) and (IV)

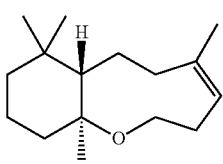
(II)

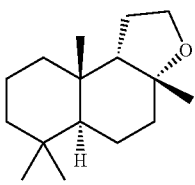
(III)

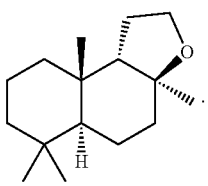
(IV)

2. A method of improving or enhancing the odour of (−)-Ambrox comprising the step of separating (−)-Ambrox from a mixture comprising one or more of the compounds (II), (III) or (IV)

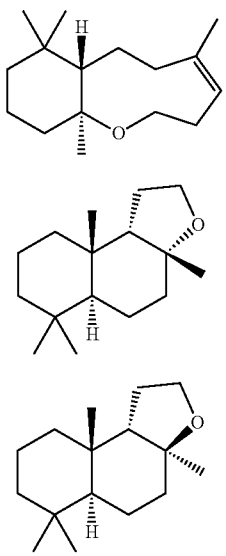

(II)

(III)

(IV)

by selective crystallization of (−)-Ambrox from the mixture, such that after the step of separating, (−)-Ambrox contains none, or only olfactory acceptable, of the compounds (II), (III) or (IV).

3. The method according to claim 1, wherein the reaction mixture is free, or is substantially free, of homofarnesol.

4. The method according to claim 1, wherein the crystallizing solvent is selected from the group consisting of water, methanol, acetone, petroleum ether, hexane, t-butyl methyl ether, THF and ethyl acetate ethanol, toluene and mixtures thereof.

5. The method according to claim 4, wherein the crystallizing solvent is an ethanol water mixture.

6. The method according to claim 1, wherein the reaction mixture is formed as a result of an enzyme-catalyzed cyclization of homofarnesol comprising a mixture of 7E,3E and 7E,3Z homofarnesol geometric isomers of homofarnesol, wherein the reaction is carried out in the presence of a recombinant microorganism expressing the gene encoding the enzyme.

7. The method according to claim 6, wherein the reaction mixture of 7E,3E and 7E,3Z homofarnesol is enriched in the 7E,3E geometric isomer.

8. The method according to claim 6, wherein the reaction mixture of 7E,3E and 7E,3Z homofarnesol consists of 7E,3E and 7E,3Z homofarnesol and no other geometric isomers of homofarnesol.

9. The method according to claim 6, wherein the weight ratio of the 7E,3E isomer to 7E,3Z isomer is at least 80:20.

10. The method according to claim 6, wherein the enzyme is a wild-type squalene hopene cyclase or a variant of the wild-type squalene hopene cyclase.

11. A perfume ingredient consisting of (−)-Ambrox and olfactory acceptable amounts of one or more of the compounds (II), (III) or (IV)

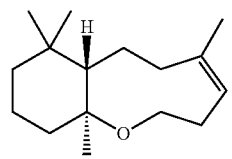

(II)

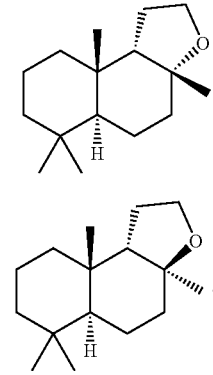

(III)

(IV)

12. The perfume ingredient according to claim 11, comprising crystalline (−)-Ambrox.

13. A perfume composition comprising (−)-Ambrox and at least one other perfume ingredient, wherein said perfume composition contains olfactory acceptable amounts of one or more of the compounds (II), (III) or (IV)

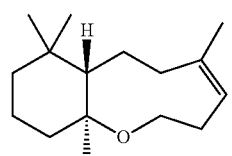

(II)

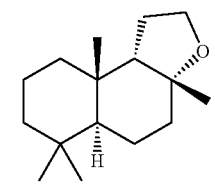

(III)

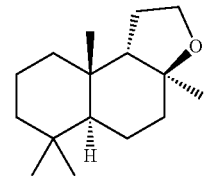

(IV)

14. The method according to claim 2, wherein the reaction mixture is free, or is substantially free, of homofarnesol.

15. The method according to claim 2, wherein the crystallizing solvent is selected from the group consisting of water, methanol, acetone, petroleum ether, hexane, t-butyl methyl ether, THF and ethyl acetate ethanol, toluene and mixtures thereof.

16. The method according to claim 15, wherein the crystallizing solvent is an ethanol water mixture.

17. The method according to claim 2, wherein the mixture is formed as a result of an enzyme-catalyzed cyclization of homofarnesol comprising a mixture of 7E,3E and 7E,3Z homofarnesol geometric isomers of homofarnesol, wherein the reaction is carried out in the presence of a recombinant microorganism expressing the gene encoding the enzyme.

18. The method according to claim 17, wherein the reaction mixture of 7E,3E and 7E,3Z homofarnesol is enriched in the 7E,3E geometric isomer.

19. The method according to claim 17, wherein the reaction mixture of 7E,3E and 7E,3Z homofarnesol consists of 7E,3E and 7E,3Z homofarnesol and no other geometric isomers of homofarnesol.

20. The method according to claim 17, wherein the weight ratio of the 7E,3E isomer to 7E,3Z isomer is at least 80:20.

21. The method according to claim 17, wherein the enzyme is a wild-type squalene hopene cyclase or a variant of the wild-type squalene hopene cyclase.

22. The method according to claim 9, wherein the weight ratio of the 7E,3E isomer to 7E,3Z isomer is at least 90:10.

23. The method according to claim 9, wherein the weight ratio of the 7E,3E isomer to 7E,3Z isomer is at least 95:5.

* * * * *